United States Patent [19]

Price

[11] 4,037,866
[45] July 26, 1977

[54] CONTACT LENS APPLICATOR

[76] Inventor: Edward E. Price, 421-B S. Marguerita, Alhambra, Calif. 91803

[21] Appl. No.: 708,862

[22] Filed: July 26, 1976

[51] Int. Cl.² .............................................. A61F 9/00
[52] U.S. Cl. .................................................. 294/1 CA
[58] Field of Search ............... 294/1 R, 1 CA, 64 R, 294/86 R; 128/303 R; 206/5.1; 351/160

[56] References Cited
U.S. PATENT DOCUMENTS

| 2,379,629 | 7/1945 | Eweson | 294/64 R |
| 2,558,479 | 6/1951 | Miller | 294/64 R X |
| 3,129,971 | 4/1964 | Kobler | 294/1 CA X |
| 3,584,908 | 6/1971 | Ray | 294/1 CA |
| 3,645,576 | 2/1972 | Horres | 294/1 CA |
| 3,879,076 | 4/1975 | Barnett | 294/1 CA |

Primary Examiner—Johnny D. Cherry
Attorney, Agent, or Firm—Herzig & Walsh Incorporated

[57] ABSTRACT

An applicator for contact lenses. A stem having a bore is provided with a flexible neoprene cap or sleeve on the end of the stem, the cap having an end wall forming a diaphragm which is configurated to have the convex side of a wet contact lens placed against it to be held by surface tension. Within the bore of the stem is a manually actuatable plunger. An opening is provided in the side wall of the stem. The lens carried at the end of the applicator can be placed adjacent the eyeball. By manually pushing in the stem, pressure is developed behind the diaphragm holding the lens to deform it and release the contact lens against the eyeball.

6 Claims, 5 Drawing Figures

CONTACT LENS APPLICATOR

BACKGROUND OF THE INVENTION

1. The Field of the Invention

The field of the invention is that of instruments or applicators for applying a contact lens to the eyeball.

2. Description of the Prior Art

Instruments or devices have been known to the prior art for applying contact lenses. Prior art patents include U.S. Pat. Nos. 2,919,696; 3,031,918; 3,091,328; 3,129,971; 3,132,887; 3,139,298; 3,645,576; and 3,743,337. Referring generally to the known prior art, typically in the known devices, they involve some type of manually held instrument or tool intended to hold the contact lens to apply it to the eyeball. The known prior art is lacking in characteristics of effectiveness, utility, and simplicity that are present in the herein invention and which are outlined in detail hereinafter.

SUMMARY OF THE INVENTION

The applicator is described in detail hereinafter in a preferred exemplary form. In the exemplary form there is provided a tubular stem having a bore with a manually actuatable plunger in the bore. The stem is enlarged at one end, the enlarged part having an enlarged counterbore with a piston in the counterbore on the end of the stem for manual actuation. These parts preferably may be made of plastic.

On the other end of the stem there is provided an end cap or sleeve made of a flexible material which may preferably be neoprene. The end portion of this end cap forms a diaphragm having an end face with a spherical configuration so that it can hold the wet convex side of a contact lens by surface tension.

A side opening or aperture is provided near the end of the tubular stem to admit pressure into the bore of the stem. When the plunger is moved in manually, the air is compressed providing pressure inside of the end cap or sleeve whereby to deform the end diaphragm so as to release the contact lens in a position wherein it is then held to the eyeball by surface tension.

The primary object of the invention is to provide an improved and extremely effective, positive acting, and simplified contact lens applicator.

A further object is to provide an applicator as in the foregoing having flexible means to hold the contact lens manually actuatable means to cause release of the lens from the actuator without physical contact with the holding diaphragm.

A further object is to provide an applicator as in the foregoing wherein a tubular stem is provided having a flexible end member including a diaphragm configurated to hold a lens by surface tension, with a manually actuatable plunger for creating pressure behind the diaphragm whereby to forceably deform it for releasing the contact lens.

Further objects and additional advantages of the invention will become apparent from the following detailed description and annexed drawings.

DESCRIPTION OF THE PREFERRED EMBODIMENT

Figure 1:
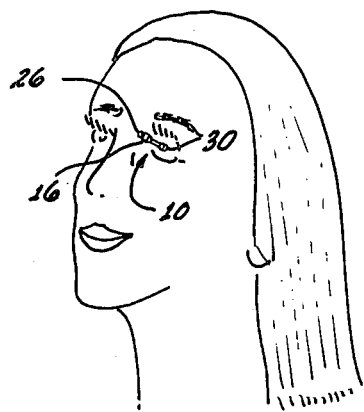
FIG. 1 is an illustrative pictorial view showing use of the applicator.

FIG. 1 illustrates use of the applicator.

Figure 2:
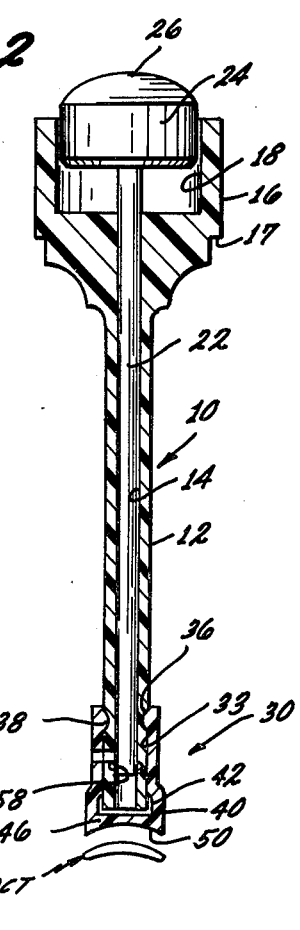
FIG. 2 is a cross sectional of a preferred form of the invention.

Referring to FIG. 2, numeral 10 designates the body of the exemplary form of the invention. The body includes a tubular stem 12 having a bore 14. At the end of the stem it is enlarged as designated at 16 and this enlarged part has an enlarged counterbore 18. The part 16 has a square annular shoulder 17.

Positioned in the bore 14 of the stem 12 is a plunger 22, the end of which extends into the counterbore 18. On the end of the plunger 22 is a piston member 24, the outer end surface of which is of spherical configuration as designated at 26. The plunger is manually operable as will be described presently.

At the opposite end of the body 10 there is provided an end cap or sleeve 30 made of a flexible material which may prefer- ably be neoprene. The end sleeve or cap 30 has a cylindrical part 32 having a bore 33 of a size to fit over the end of the stem 12. Inside of the end of the bore 33 there is formed an annular rib 36, the surface of which is of rounded configuration. At this poiont in stem 12 there is formed an annular grove 38 of the same cross-sectional configuration so that the rib 36 can fit into it holding the end cap 30 in place.

The outer end of the cap 30 is of slightly larger outer diameter as designated at 40 and the inner diameter of this part of the cap is of slightly larger diameter as designated at 42. The end part of cap 30 is designated at 46. It forms an end wall or diaphragm slightly spaced as shown from the end end the stem 12. The outer surface of the end wall or diaphragm is of spherical configuration or conformation as designated at 50.

In a side wall of the tube 12 near the end is an aperture or port as designated at 52 and it is aligned with a similar port 54 formed in the side of the cap 30. These ports are for the purpose of admission of air into the bore 14 as will be described hereinafter.

In the end part of stem 12 in an annular groove 56 with O-ring 58 for sealing purposes.

Figure 5:
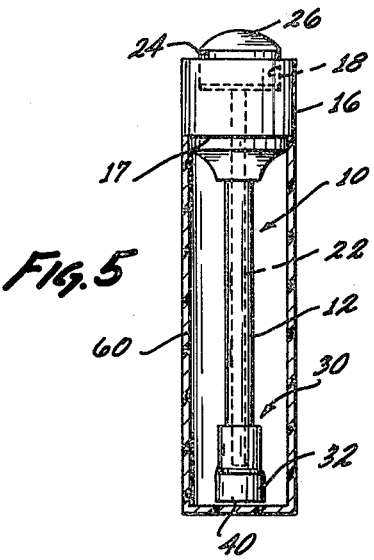
FIG. 5 is a view showing the applicator in a container.

The applicator may be carried in a cylindrical container 60 as shown in FIG. 5 which fits against square shoulder 17 on end part 16.

OPERATION

Figure 3:
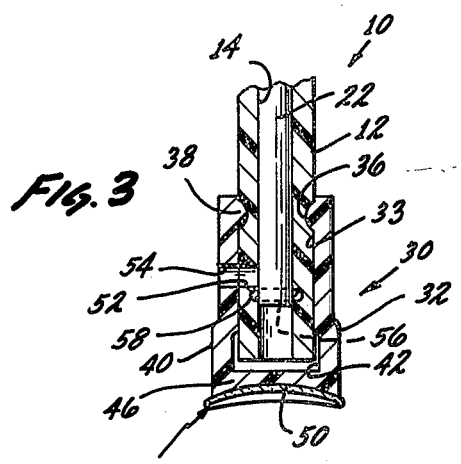
FIG. 3 is a cross sectional view of the end of the applicator shown holding a lens.
Figure 4:
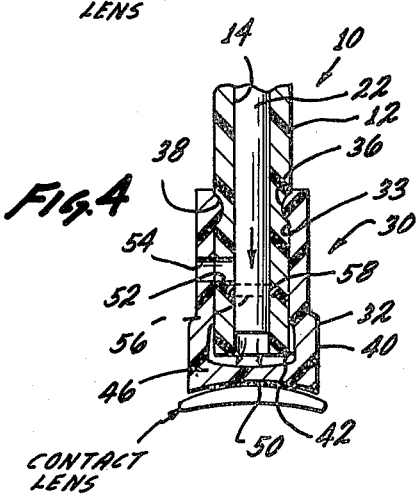
FIG. 4 is a cross sectional view of the end of the applicator illustrating positioning of the lens.

In the operation or utilization of the applicator a contact lens is moistened and the spherical side of the contact lens is placed against the spherical surface 50 of the diaphragm 46 which is held by surface tension. The applicator, while then being held in the hand between the fingers, can be maneuvered and positioned so as to position the contact lens against the eyeball. The plunger stem 22 is pulled outwardly slightly by the piston or knob 24 to allow air to enter through the ports 52 and 54 into the bore 14 and into the interior of the end part of the cap 30, that is, within the enlarged end part 40. When the lens is properly positioned against or adjacent to the eyeball as illustrated in FIG. 1, the plunger stem 22 is then pushed in slightly manually so as to compress the air within the end part 40 of the cap and in back of the diaphragm 46, see FIGS. 3 and 4. Since the diaphragm portion of the cap is flexible, pressure causes it to deform to change the curvature of the surface 50 to thereby break the surface tension and release the contact lens which is then held by surface tension against the eyeball.

Thus, it is to be seen that although the device is very small, the contact lens can be very positively held by it without danger of the lens dropping off and being lost, it being a matter of common knowledge that contact lenses are extremely expensive. The applicator can be very readily and easily manipulated or moved so as to position the contact lens against the eyeball. Release of the lens from the applicator can be very effectively realized by pushing in the plunger stem to create the pressure behind the diaphragm for deforming it.

From the foregoing, those skilled in the art will readily understand the nature of the invention and the manner in which all of the objects as set forth in the foregoing are realized. The device can be fabricated very economically from relatively inexpensive material and without resort to expensive or complex manufacturing techniques. Even though the parts are of a relatively simple nature, the applicator is extremely effective for its purpose and is easy and simple to use.

The foregoing disclosure is representative of a preferred form of the invention and is to be interpreted in an illustrative rather than a limiting sense, the invention to be accorded the full scope of the claims appended hereto.

What is claimed is:

1. An applicator instrument for use with a contact lens comprising a flexible member having a portion configurated to be in contact with the convex surface of a contact lens for holding it by surface tension, means carrying the said member adpated to be positioned wwhereby a contact lens can be applied to a position against an eyeball, and means for deforming the flexible member whereby to release the contact lens leaving it against the eyeball.

2. An instrument as in claim 1, wherein said carrying means includes a stem, the flexible member being mounted at the end of the stem and said deforming meams including whereby a force can be applied to a part of the flexible member for deforming it.

3. An instrument as in claim 2, wherein said stem has a bore therethrough, said flexible member being formed as a cap on the end of the stem and said deforming means including means for pressurizing the interior of the stem whereby to apply pressure against the flexible member portion for deforming it.

4. An instrument as in claim 3 wherein said deforming means includes a plunger movable in the bore of said stem for producing pressure in the bore for providing force to act on the flexible member.

5. An instrument as in claim 4, wherein the said stem includes an enlargement at one end having an enlarged bore therein, with a manually actuatable member movable in the enlarged bore and carried on the end of the plunger.

6. An instrument as in claim 4, wherein said cap and said stem having registering parts therein to allow air to enter the bore in the stem ahead of said plunger.

* * * * *